US005662894A

United States Patent [19]
McManus

[11] Patent Number: 5,662,894
[45] Date of Patent: *Sep. 2, 1997

[54] SUNSHIELD SHAVING COMPOSITIONS

[76] Inventor: JT McManus, P.O. Box 4021, Carson City, Nev. 89702

[*] Notice: The portion of the term of this patent subsequent to Feb. 3, 2013, has been disclaimed.

[21] Appl. No.: 101,524

[22] Filed: Aug. 3, 1993

[51] Int. Cl.$^6$ .................................................. A61K 7/15
[52] U.S. Cl. ......................................... 424/73; 424/401
[58] Field of Search ............................. 424/73, 59, 401, 424/70.9; 514/469

[56] References Cited

U.S. PATENT DOCUMENTS

| | | | |
|---|---|---|---|
| 4,454,112 | 6/1984 | Tuominen | 424/60 |
| 4,563,346 | 1/1986 | Deckner | 424/73 |
| 4,603,046 | 7/1986 | Georgalas et al. | 424/59 |
| 4,900,541 | 2/1990 | Govier | 424/59 |
| 4,917,882 | 4/1990 | Strobridge | 424/59 |
| 4,999,186 | 3/1991 | Sabatelli et al. | 424/59 |
| 5,008,100 | 4/1991 | Zecchino et al. | 424/59 |
| 5,008,101 | 4/1991 | Klimisch et al. | 424/60 |
| 5,026,540 | 6/1991 | Dixon et al. | 424/59 |
| 5,034,213 | 7/1991 | Rosenbaum et al. | 424/60 |
| 5,041,281 | 8/1991 | Strobridge | 424/47 |
| 5,087,445 | 2/1992 | Haffey et al. | 424/59 |
| 5,093,107 | 3/1992 | Matravers | 424/59 |
| 5,138,089 | 8/1992 | Sabatelli et al. | 560/50 |
| 5,145,669 | 9/1992 | Kwak et al. | 424/59 |
| 5,152,983 | 10/1992 | Nambudiry et al. | 424/60 |
| 5,160,731 | 11/1992 | Sabatelli et al. | 424/59 |
| 5,169,624 | 12/1992 | Ziegler et al. | 424/59 |

OTHER PUBLICATIONS

DeSimone, "Suncreen and Suntan Products", *Handbook of Non-prescription Drugs*, 7th Ed., Chapter 26, pp. 499–511 (American Pharmaceutical Association, Washington, D.C.; 1982).

Grove and Forbes, "A Method for Evaluating the Photoprotection Action of Sunscreen Agents Against UV-A Radiation", *International Journal of Cosmetic Science*, 4, pp. 15–24 (1982).

*Primary Examiner*—Thurman K. Page

[57] ABSTRACT

The use of sunscreen related compounds for hair removal.

4 Claims, No Drawings

SUNSHIELD SHAVING COMPOSITIONS

FIELD OF INVENTION

This invention relates to the novel new use of a sunscreen composition means to facilitate the removal of hair from the body with a shaving means as well as provide continued skin conditioning and protection from the harmful radiation of the sun after the hair removal process is complete.

BACKGROUND OF THE INVENTION

The removal of hair from the human epidermis is commonly accomplished by shaving with a mechanical means such as a razor blade or power shaver designed to be used under wet conditions. Hair removal for the human male is a daily exercise to remove facial hair, and for the human female is a regular, but less frequent exercise generally to remove hair from the body such as the legs and underarms.

There are a number of compositions available to facilitate removing hair from the body with the use of mechanical means. Some compositions perform as a pre-shave, to prepare the hair to be removed; as a during-shave, to lubricate the skin and facilitate shaving; and as an after-shave to condition the skin and add fragrance to the area shaved.

A wide variety of soaps, creams and oils are available to facilitate the shaving process. However, in general they cause discomfort and trauma to the skin. Shaving creams are, by far, the preparation of choice for facilitating the shaving process for lessening the abrasion, irritation, and localized trauma which, to a greater or lesser extent, is associated with hair removal by shaving. Shaving creams are lather-producing, either through the action of a brush or as propelled from an aerosol container. Both are commonly formulated using soap and/or detergents as the lather forming composition. The lather or brushless shaving cream are oil-in water emulsions of the cream type.

Shaving cream is also commonly a lather-forming, soap-based formulation further modified for application with a shaving brush or as a soap-based and/or detergent foam from an aerosol dispenser. Such formulations provide an easy and rapid production of copious lather which is supposed to be resistant to collapse; should hold the hair erect; should provide sufficient lubrication for the razor blade and there should be minimum irritation of the skin.

The treatment of human skin with various compositions has been undertaken for many years with the goal being to keep the skin in a smooth supple condition. Skin has the tendency to dry out when exposed to conditions of low humidity or to extended periods in detergent. These considerations have not been adequately taken into consideration when shaving preparations are proposed.

Shaving lotions have generally been prepared with regard to the hair follicles only so as to prepare the hair for cutting by a razor. Silicone products have been introduced in order that a razor may travel more easily on the skin without nicking. None of the products provide any beneficial features to the skin. In fact, most commercial products contain ingredients which cause denaturization or other harmful effects. Shaving preparations containing detergents or soap products or one of such deleterious products, are commonly utilized today. It is only after the shaving process that any concern is made for conditioning the skin. In many cases even those products cause damage and trauma to the skin.

The damaging effects of sunlight on skin are well documented. Damage from excessive UV exposure can occur by sunbathing as well as routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e. sunburn). The 290 to 320 nanometer wavelength ultraviolet radiation range, designated as the "UVB" wavelength range, tends to be the primary cause of erythema. The 320 to 400 nanometer wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982) and Grove and Forbes, "A Method for Evaluating the Photoprotection Action of Sunscreen Agents Against UV-A Radiation" *International Journal of Cosmetic Science*, 4, pp. 15–24 (1982); the disclosures of all of which are incorporated herein by reference. Hence, although the immediate effects of ultraviolet radiation may be cosmetically and socially gratifying, the long-term hazards are cumulative and potentially serious.

The fact that these effects are taken seriously by the general public is suggested by considering the market for sun protection products. This market has grown considerably in recent years and many new products are introduced each year. What used to be looked upon as a seasonal business is now continuous. Sun protection compositions are now included in a diversity of personal care products, particularly cosmetic-type products for women, which are worn on a daily basis. The human face is exposed to sun radiation more than any other part of the human body; especially in the case of men. Men are becoming more aware of the necessity to wear sun protection compositions on a daily basis.

To remove hair from the body with a razor blade or power shaver designed to be used in wet conditions, one usually applies a pre-shave composition to the area to prepare the hair as well as lubricate the area to facilitate shaving, cut off the hair, wash off the pre-shave composition, apply an after-shave or skin conditioning composition. A sunscreen composition may at some point be applied to the area shaved.

From the foregoing, it is evident that the requirements of a preferred cream with the necessary properties to facilitate shaving on the one hand but formulated from non-irritating chemicals presents a problem of considerable dimension to those skilled in the art. This is partially due to a misunderstanding of what is necessary to affect a close, comfortable, effective non-irritating shave.

From the foregoing it is also evident that the requirements of a preferred sunscreen with the necessary properties to protect one from the harmful effects of radiation on a daily basis is also necessary.

SUMMARY OF THE INVENTION

This invention relates to a new and simpler use of a sunscreen composition means as a facilitating means for removal of hair from a human or other animal, with a shaving means, whereby a residual of said sunscreen composition means remains on the skin, until washed off or it wears off, as a means of providing continued protection from the harmful radiation of the sun as well as from ultraviolet radiation from sources other than the sun.

Using a sunscreen composition as a shaving composition to facilitate hair removal as described in applicants invention, has at least the following objects and advantages:

1. Provides a new means of removing hair from the body;
2. provides a skin care preparation which can be utilized as a shaving composition;
3. facilitates shaving with a mechanical means;
4. provides a simpler means of shaving;
5. provides lubrication to the area shaved;
6. provides a lubricating means as a beneficial means to the skin and a shaving means to facilitate shaving;
7. provides a comfortable shave;
8. provides moisturizing to the skin;
9. provides softening to the skin;
10. conditions the skin to help keep it supple;
11. a means, allowing fewer chemicals to be applied to the skin;
12. eliminates the need of harmful soap, detergents, shaving gels, and similar shaving compositions;
13. eliminates the harmful effects soap, detergents, shaving gels and similar shaving compositions means have on the skin;
14. provides a sunscreen composition which can be easily and conveniently applied before or after shaving;
15. provides a means of continued sunscreen protection from the harmful radiation of the sun as well as from ultraviolet radiation from sources other than the sun, after shaving is finished;
16. may be made with a typical sun protection factors;
17. provides healthful advantages by protecting the skin from the harmful radiation of the sun and thereby helping to reduce the possibility of skin cancer;
18. has ecological advantages by requiring fewer products and containers to be manufactured;
19. has economical advantages by eliminating the necessity of purchasing several different shaving products.
20. Acts as a lubricating means which effectively extends the utility of the shaving means.

Further objects and advantages will become apparent upon reading the descriptions herein.

DESCRIPTION OF INVENTION

"Composition(s)" is used herein in place of the phrase "liquid, lotion, oil, or similar compositions" normally applied to the body.

"Sunscreen" includes any composition applied to the body for the purpose of providing skin protection from the harmful radiation of the sun.

The use of the compositions described here provide a smooth comfortable shave; that does not have the harsh, drying, and tightening effects of the skin that typically accompany shaving soaps, detergents, gels, and similar compositions available on the market. It has been discovered that compositions normally found in sunscreen surprisingly have the necessary emollients and skin conditioners to facilitate hair removal. Further, they provide the continued skin conditioning and protection from the harmful radiation of the sun needed after the shaving process is finished.

Through experiment, it was discovered that it is not necessary to use soap or detergents to shave; it is not necessary to have a foam or lather to shave; it is not necessary to have a lather that is resistant to collapse; it is not necessary to soften the hair in a viscosity sufficient to hold the hair erect to shave, as is commonly claimed to be the case. Sufficient lubrication to allow the razor blade to glide smoothly over the skin providing minimum razor irritation and a shaving composition that does not cause irritation to the skin are important. It was discovered that sunscreen compositions as well as moisturizing compositions with a sunscreen additive, when applied prior to shaving, have the necessary skin conditioners and emollients to protect the skin, prepare the hair, lubricate the area and facilitate shaving thereby providing a close, smooth, and comfortable shave without the harsh effects of other shaving compositions; and after the shaving process is finished the sunscreen composition provides continued protection from the harmful radiation of the sun.

A variety of sunscreen compositions can be purchased over the counter in local stores for the necessary skin conditioning and shaving requirements.

Any sunscreen compositions with any sun protection rating factor typically available can be used. For example, the ingredients of a moisturizing sunscreen composition tested, with an SPF (Sun Protection Factor) of 8, consisted of Ethylhexyl P-methoxycinnamate, 2-ethylhexyl salicylate, oxybenzone and other ingredients; the ingredients of one sunscreen composition tested, with an SPF of 8, consisted of octyl dimethyl PABA, oxybenzone, benzyl alcohol, carbomer 943, carbomer 941, dimethicone, disodium EDTA, fragrance, glyceryl stearate, isotearic acid, mineral oil quaternium-15 stearyl alcohol, water, and other ingredients; and another sunscreen composition tested, with an SPF of 25, consisted of Octyl methoxycinnamate, benzophenone-3, homosalate, menthyl anthranilate, octyl salylate; yet another sunscreen composition tested, with an SPF of 8, consisted of BHT, C12–15 alcohols benzoate, carbomer, cetyl alcohol, DEA cetyl phosphate, dimethicone, dioctyl sodium sulfosuccinate, disodium EDTA, fragrance, glyceryl dilaurate, isopropyl isostearate, isopropyl PPG-2-isodeceth-7 carboxylate, isotearic acid, propylene glycol, quaternium-15, simethicone, tocopheryl acetate, water, and other ingredients; and yet another sunscreen tested, with an SPF of 15, consisted of Octyl methoxycinnamate, octyl salicylate oxbenzone, titanium dioxide, barium sulfate, benzyl alcohol, C12–15 alcohols benzoate, carbomer 941, dimethicone, disodium EDTA, fragrance, glycerin, glyceryl stearate, isotearic acid, mineral oil, quaternium-15, stearic acid, stearoxytrimethylsilane, stearyl alcohol, tocapheryl acetate, water and other ingredients. A large number of sunscreen lotions with different compositions and SPF ratings (from 2 to 45) were tested and found to function equally well. The choice of the composition is dependant only on user preference. The inventor prefers an SPF of 8 to 15 for 8 to 15 hours of sun protection.

Sunscreen compositions are available from Perrigo, Allegan, Mich.; Almay, Inc., New York, N.Y.; Proctor & Gamble Co., Cincinnati, Ohio; Cumberland-Swan, Smyrna, Tenn.; Schering-Plough, Memphis, Tenn.

Any sunscreen formulation having an SPF of 2 or greater in a pharmaceutically-acceptable carrier can be employed.

The sunscreen compositions for the present invention would contain a pharmaceutically-acceptable sunscreen carrier. The term "pharmaceutically-acceptable sunscreen carrier", as used herein, means one or more substantially non-irritating compatible filler diluents which are suitable for topical application to the skin of a human or lower animal. The term "compatible" as used herein, means that the components of the carrier must be capable of being commingled with the sunscreen composition, and with each other, in a manner such that there is no interaction which could substantially reduce the efficacy of the composition during use for protecting the skin from the effects of UVA and UVB wavelength radiation. Pharmaceutically-acceptable sunscreen carriers must, of course, be of sufficiently high purity and sufficiently low toxicity to render them suitable for topical administration to a human or lower animal.

The sunscreen compositions of the present invention should contain a pharmaceutically-acceptable sunscreen carrier selected as appropriate for the formulation desired. For example, it is possible to prepare sunscreen compositions for the present invention in the form of organic solvent solutions, aqueous emulsions, gels, or aerosol formulation. Preferred are sunscreen compositions of those formulated as aqueous emulsions. Said pharmaceutically-acceptable sunscreen carriers useful in the compositions include, for example, water, oils, fats, waxes, synthetic polymers, emulsifiers, emollients, sufactants, perfumes, dyes, preservatives, artificial tanning compositions (e.g., dihdroxyacetone), and conventional sunscreening compositions (e.g., octyl N,N-dimethyl-paraaminobenzoate; 2-hydroxy-4-methoxybenzophenone).

Types of emulsifiers useful in the sunscreen compositions of the present invention include ethoxylated fatty acids, ethoxylated esters, ethoxylated ethers, ethoxylated alcohols, phosphated esters, polyoxyethlylene fatty ether phosphates, fatty acid amedes, acyl lactylates, soaps and mixtures thereof. Fatty alcohols such as cetyl and sterayl alcohol, and cetearyl alcohol are also regarded as emulsifiers for purposes of the present invention.

There are many ways the products of the invention may be utilized before, during, and/or after the shaving process is finished.

An application of the present invention is with the use of a mechanical shaving means such as a razor blade shaver or power shaver designed to be used in wet conditions. A sunscreen/shaving composition is applied as a coating to the area, in an amount effective, to condition the skin and lubricate the area to facilitate removing hair, as well as provide continued skin conditioning and protection from the harmful radiation of the sun after the shaving process is finished. Said sunscreen/shaving composition should be applied in an amount sufficient to cover the area to be shaved to condition the skin and to facilitate smooth and comfortable shaving. The coating used will depend on personal preferences. When finished shaving, the residual of said sunscreen/shaving composition should be spread over the area shaved and massaged into the skin. Said sunscreen/shaving composition may contain any sun protection factor rating the user desires. Said sunscreen/shaving composition may or may not have skin fragrancing, skin moisturizing, or other additives. harmful radiation of the sun. Said sunscreen/shaving composition is applied to the area after hair removal in an amount sufficient to cover the area and provide protection from the harmful radiation of the sun. Said sunscreen/shaving composition may also be used by people who do not shave for the purpose of providing sunscreen protection, skin conditioning, fragrancing, and the like to their skin.

The above described applications are not intended to limit the use of the herein described invention, but are meant to provide a guide to its many uses. The description of this new use invention disclosed herein is intended to include all of those improvements, variations and compositions which would be obvious to those skilled in the art of developing, manufacturing and selling sunscreen, moisturizing, shaving, pre-shave and after-shave products.

What is claimed is:

1. A process providing hair removal, sunscreen protection and skin conditioning to the skin which comprises the topical application of a shaving formulation comprising a sunscreen agent, a carrier selected from the group consisting of an organic solution, a gel and an aerosol, an emulsifier in an amount sufficient to provide lubricity to the skin, followed by the application of a mechanical shaving means for a period of time until the skin is shaved, said process leaving a coating on the skin which is subsequently massaged in the skin.

2. The invention of claim 1, whereby said formulation is in the form of an aqueous emulsion.

3. The invention of claim 1, whereby said formulation is a pharmaceutically acceptable composition.

4. The invention of claim 1, whereby said formulation provides fragrance to the skin.

* * * * *